(12) United States Patent
Gerard

(10) Patent No.: US 12,276,649 B2
(45) Date of Patent: Apr. 15, 2025

(54) METHOD FOR DISPLAYING CONCENTRATION DATA OF A SUBSTANCE AND AN ASSOCIATED APPARATUS

(71) Applicant: INFICON, Inc.

(72) Inventor: Elliot Gerard, Hialeah, FL (US)

(73) Assignee: Inficon Inc., East Syracuse, NY (US)

( * ) Notice: Subject to any disclaimer, the term of this patent is extended or adjusted under 35 U.S.C. 154(b) by 0 days.

(21) Appl. No.: 18/533,823

(22) Filed: Dec. 8, 2023

(65) Prior Publication Data

US 2024/0102982 A1 Mar. 28, 2024

Related U.S. Application Data

(63) Continuation of application No. 16/973,488, filed as application No. PCT/US2019/040248 on Jul. 2, 2019, now Pat. No. 11,841,354.

(60) Provisional application No. 62/693,733, filed on Jul. 3, 2018.

(51) Int. Cl.
*G01N 33/00* (2006.01)
*G01M 3/16* (2006.01)

(52) U.S. Cl.
CPC .......... *G01N 33/0067* (2013.01); *G01M 3/16* (2013.01); *G01N 33/0008* (2013.01); *G01N 33/0063* (2013.01)

(58) Field of Classification Search
None
See application file for complete search history.

(56) References Cited

U.S. PATENT DOCUMENTS

| 5,447,055 | A | * | 9/1995 | Thompson | G01M 3/226 73/23.35 |
| 5,861,547 | A | | 1/1999 | Kawai et al. | |
| 6,035,701 | A | * | 3/2000 | Lowry | E02D 1/00 405/129.1 |
| 6,182,497 | B1 | * | 2/2001 | Krajci | H04Q 9/00 73/40.5 R |

(Continued)

FOREIGN PATENT DOCUMENTS

| BR | 112020025644 A2 | 3/2021 |
| BR | 112020026901 A1 | 3/2021 |

(Continued)

OTHER PUBLICATIONS

JP Patent Application No. 2021-500028, filed Jul. 7, 2019; Notice of Rejection; Dispatch Date Feb. 20, 2024 (6 pages).

(Continued)

*Primary Examiner* — Daniel S Larkin
(74) *Attorney, Agent, or Firm* — Barclay Damon LLP

(57) ABSTRACT

A method for displaying gas concentration values on a graphical display of a leak detector comprises detecting a presence of a gas using a gas sensor. A signal is generated by the gas sensor and transmitted from the gas sensor to a processor. The received signal is processed to determine a gas concentration value and a corresponding time stamp. The gas concentration values and corresponding time stamps are displayed graphically as they are determined and newly determined gas concentration values and corresponding time stamps are displayed in relation to previously determined gas concentration values and time stamps in streaming manner.

13 Claims, 13 Drawing Sheets

(56) References Cited

U.S. PATENT DOCUMENTS

| | | | | |
|---|---|---|---|---|
| 7,051,578 | B2* | 5/2006 | McCoy | G01M 3/229 |
| | | | | 73/40.7 |
| 7,710,568 | B1* | 5/2010 | Paige | G01J 3/0272 |
| | | | | 356/73 |
| 8,330,605 | B2* | 12/2012 | Johnson, Jr. | G01N 33/0075 |
| | | | | 340/3.1 |
| 9,201,035 | B2* | 12/2015 | Chuang | G01N 27/12 |
| 9,500,556 | B2* | 11/2016 | Rella | G01N 21/3504 |
| 2011/0016885 | A1* | 1/2011 | Zhang | F25B 21/00 |
| | | | | 62/3.1 |
| 2011/0025800 | A1* | 2/2011 | Rosati | B41J 2/175 |
| | | | | 347/104 |
| 2011/0161885 | A1* | 6/2011 | Gonia | G08B 21/12 |
| | | | | 715/764 |
| 2011/0251800 | A1* | 10/2011 | Wilkins | G01S 19/49 |
| | | | | 702/24 |
| 2013/0328697 | A1* | 12/2013 | Lundy | G08C 17/02 |
| | | | | 340/870.01 |
| 2014/0026641 | A1* | 1/2014 | Rella | G01N 21/3504 |
| | | | | 73/30.01 |
| 2016/0307468 | A1* | 10/2016 | Trumbull | G09B 5/02 |

FOREIGN PATENT DOCUMENTS

| | | | | |
|---|---|---|---|---|
| BR | 112021000063 | A2 * | 4/2021 | G01M 3/18 |
| BR | 112021000111 | A2 | 4/2021 | |
| BR | 112021000806 | A2 * | 4/2021 | G01V 1/003 |
| BR | 112021001111 | A2 * | 4/2021 | G21C 3/58 |
| BR | 112021001382 | A2 * | 4/2021 | G02B 27/0093 |
| BR | 112021001584 | A2 * | 4/2021 | B03C 3/025 |
| BR | 112021002059 | A2 * | 5/2021 | C09K 11/00 |
| BR | 112021002157 | A2 * | 5/2021 | A61K 31/198 |
| BR | 112021002386 | A2 * | 5/2021 | |
| BR | 112021004133 | A2 * | 5/2021 | G02B 6/2861 |
| BR | 112021005652 | A2 * | 6/2021 | B67D 1/0412 |
| CN | 104507733 | A | 8/2015 | |
| JP | 4009633 | B2 | 1/1992 | |
| JP | 07174673 | A | 7/1995 | |
| JP | 2005083949 | A | 3/2005 | |
| JP | 2006135760 | A * | 5/2006 | |
| JP | 2013079832 | A | 5/2013 | |
| JP | 2014035300 | A | 2/2014 | |
| JP | 2015056060 | A | 3/2015 | |
| JP | 2015532437 | A | 11/2015 | |
| WO | 03/016851 | A1 | 2/2003 | |
| WO | 2015123622 | A1 | 8/2015 | |
| WO | 2017097711 | A | 6/2017 | |

OTHER PUBLICATIONS

JP Patent Application No. 2021-500028, filed Jul. 7, 2019; English translation of Notice of Rejection; Dispatch Date Feb. 20, 2024 (9 pages).

CNIPA, Office Action from corresponding Chinese Patent Application No. 201980044507.8, mailed Dec. 1, 2023.

PCT/US2019/40248, International Filing Date Jul. 2, 2019, International Search Report and Written Opinion, Date of Mailing Sep. 24, 2019 (9 pages).

PCT/US2019/40248, International Filing Date Jul. 2, 2019, International Preliminary Report on Patentability, Dated Jan. 5, 2021 (7 pages).

Instituto Nacional Dapropriedade Industrial (INPI); Office Action from Brazilian Patent Application No. BR112020025644-7; mailed Jun. 1, 2023 (in Portuguese) 4 pages.

BR 112020025644-7; Filing Date Jul. 2, 2019; Informal Translation of Preliminary Office Action, Mailed Aug. 23, 2022; 1 page.

BR 112020025644-7; Filing Date Jul. 2, 2019; Preliminary Office Action, Mailed Aug. 23, 2022; 6 pages.

European Patent Office; Application No. 19830164.0; Dated Sep. 16, 2024; 5 pages.

Mexican Patent Office; Application No. MX/A/2020/013687; Dated: Jun. 10, 2024; 3 pages.

Intellectual Property of India; Examination Report; Application No. 202037052781; Dated: Oct. 19, 2022.

CNIPA, Office Action from corresponding Chinese Patent Application No. 201980044507.8, Issued: Jan. 13, 2025.

* cited by examiner

METHOD FOR DISPLAYING CONCENTRATION DATA OF A SUBSTANCE AND AN ASSOCIATED APPARATUS

CROSS-REFERENCE TO RELATED APPLICATIONS

This application is a continuation of U.S. patent application Ser. No. 16/973,488, filed on Dec. 9, 2020, now U.S. Pat. No. 11,841,354, which is a national phase application of PCT Application No. PCT US2019/040248, filed on Jul. 2, 2019, which claims priority to, and the benefit of, U.S. Provisional Application No. 62/693,733, filed on Jul. 3, 2018. The entire contents of said applications are hereby incorporated by reference.

TECHNICAL FIELD

This application is directed generally to the field of leak detection and more specifically to a portable device that measures the concentration of a substance and displays the results graphically to assist the user in locating or pinpointing the source of a substance leak.

BACKGROUND

Leaks involving the release of substances, such as combustible gases, or otherwise toxic gases can be very dangerous. Specifically, the release of refrigerant gases are a major concern due to their harmful effects on the climate. Ozone depleting gases, such as chlorofluorocarbons (CFCs), and gases with high global warming potentials (GWP), such as hydrochlorofluorocarbons (HCFC's) and hydrofluorocarbons (HFC's), are subject to strict legislative restrictions that require leaks in systems containing these gases to be quickly located and repaired. Other systems use hydrofluoroolefins (HFO's), which are low GWP gases that are used to replace HCFC's and HFC's and are not subject to the same environmental restrictions. However, quickly locating and repairing leaks in HFO systems is also critical, especially due to the much higher cost of HFO's as compared to HCFC's and HFC's.

Currently, portable gas leak detectors are used to help find the source of gas leaks, however they are plagued by several problems that impede the user from quickly and accurately finding the leak source. For example, substantial air movement in the area of the leak may affect detector readings or the area near the leak may be significantly contaminated with gas, which causes the detector to respond in an area away from the actual leak source.

Over the years improvements to leak detectors have been made including equipping leak detectors with highly sensitive sensors that are capable of sending and responding to very low concentrations of gas. This is especially beneficial when searching for a leak in a windy environment. Other leak detectors are programmed to automatically "zero" the sensor signal to the ambient to overcome areas where gas concentration is high thereby allowing the user to pinpoint an area closer to the leak source than would normally be possible.

These are just some of the shortcomings of leak detectors currently in use.

SUMMARY

A method for displaying gas concentration values on a graphical display of a leak detector comprises detecting a presence of a gas using a gas sensor, generating a signal from the gas sensor and transmitting the signal from the gas sensor to a processor. The signal is processed to determine a gas concentration value and a corresponding time stamp, which is stored. The transmitted signals are monitored over a predetermined time period. The gas concentration values and corresponding time stamps are displayed graphically as they are determined with newly determined gas concentration values and corresponding time stamps displayed in relation to previously determined gas concentration values and time stamps in a streaming fashion.

An embodiment of a gas leak detector comprises a gas sensor configured to generate a signal in response to a presence of gas and a processor in communication with the gas sensor and configured to receive the signal generated by the gas sensor and convert the signal to gas concentration data. The processor is further configured to continuously monitor the signal over a predetermined time period. A memory unit in communication with the processor and configured to store gas concentration data such that the stored gas concentration data can be accessed by the processor. A display in communication with the processor and configured to display gas concentration data as it is obtained, wherein newly obtained gas concentration data is displayed graphically along with previously displayed gas concentration data in a streaming manner.

The disclosed embodiments improve upon the problems with the prior art by providing apparatus, systems and methods to display a real-time indication of the gas sensor's response to changes in concentration over a specified time period. As the leak detector ("detector") sweeps or scans a suspected area, the trace on the display screen also sweeps or scans across the display so that a user can more easily detect the leak through spikes in gas concentration measured by the detector. The present invention provides a display illustration displaying small and/or rapid changes that can instantly alert the user of any change in gas concentration. The present invention provides the user with a much higher resolution than the conventional display by showing the raw signal or data directly from the gas sensor with limited hardware/software interface including preset triggers that are required for the conventional bar graph or numerical displays.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein.

DETAILED DESCRIPTION

Figure 1:
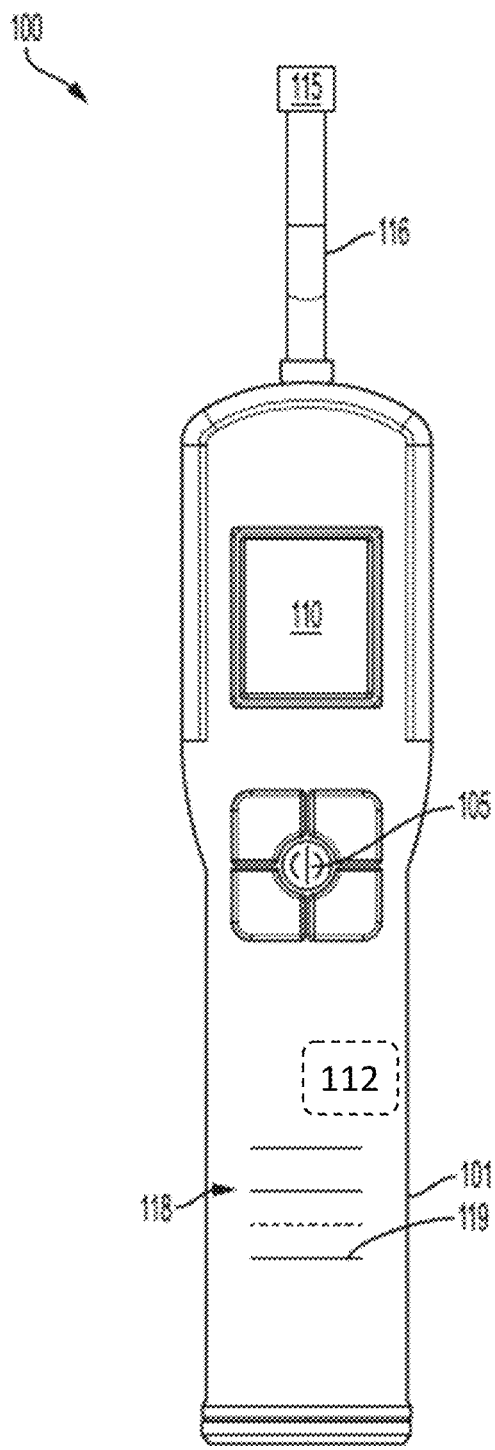
FIG. 1 illustrates a top perspective view of an embodiment of a leak detector.

The following detailed description refers to the accompanying drawings. Whenever possible, the same reference numbers are used in the drawings and the following description to refer to the same or similar elements. It will be understood that the herein described versions are examples that embody certain inventive concepts as detailed herein. To that end, other variations and modifications will be readily apparent to those of sufficient skill. In addition, certain terms are used throughout this discussion in order to provide a suitable frame of reference with regard to the accompanying drawings. These terms, such as "upper", "lower", "forward", "rearward", "interior", "exterior", "front", "back", "top", "bottom", "inner", "outer", "first", "second", and the like, are not intended to limit these concepts, except where so specifically indicated. The terms "about" or "approximately" as used herein may refer to a range of 80%-125% of the claimed or disclosed value. With regard to the drawings, their purpose is to depict salient features of the system, method and device for displaying concentration data of a substance and are not specifically provided to scale.

Current gas detectors still do not allow for easy and fast detection of a gas leak. One of the main shortcomings that still exists with the current portable gas leak detectors is that the detected gas concentration is displayed using a numerical value or a bar graph type indication. Accordingly, the concentration value displayed by the leak detector only gives the user a brief momentary snapshot of a change in gas concentration. This snapshot does not track or simulate the user's actual sweeping or scanning motion of the leak detector probe while searching for the leak source and therefore, fails to accurately pinpoint the location of a gas leak. Moreover, existing gas leak detectors also do not have the ability to detect small and/or rapid changes in the baseline of the trace or the ambient environment that can instantly alert the user of a change in gas concentration.

Figure 2:
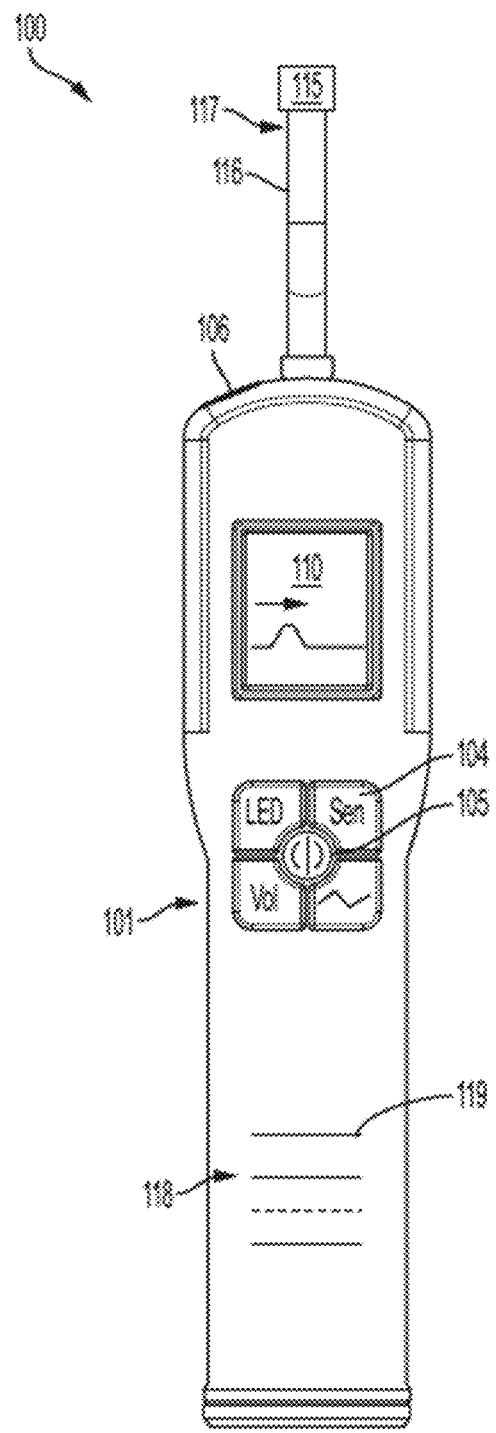
FIG. 2 illustrates a top perspective view of an embodiment the leak detector.

Referring to FIGS. 1-2, an embodiment of a portable gas leak detector, herein referred to as a detector 100, generally comprises a housing 101, a user interface 105, a display 110, and a gas sensor 115. As shown, the detector 100 may further comprise a probe 116 extending from the housing and configured to support or otherwise couple to the gas sensor 115 at a free end 117. The housing 101 is configured so that it may easily be handled or grasped in a user's hand. In an embodiment, the housing 101 may have a contact zone or contact portion 118 that may define one or more surface features 119 configured to facilitate grasping and/or holding of the detector 100.

As shown in the embodiment of FIG. 2, the user interface 105 may comprise controls for on/off functions, volume, contrast, brightness, selection of data display modes, data sensitivity levels, a timer, and any other suitable parameters that aid in the display function of the user interface 105 or operation of the detector 100. One or more lights 106 may be included on the detector 100. The one or more lights 106 may comprise an explosion-proof light emitting diode (LED) or any other light source 106 that is explosion proof when exposed to a combustible gas. In another embodiment, the one or more lights 106 may not be explosion-proof such that the detector 100 may only be used in situations where the gas to be detected is noncombustible. In an embodiment, the user interface 105 comprises a plurality of buttons 104, however in other embodiments, the user interface 105 may comprise a touch screen. Still other embodiments of the user interface 105 may comprise switches, toggles, and other such features may also be used and are within the spirit and scope of the present invention.

The display 110 is configured to show the measured gas concentration values in graphical form as illustrated in FIGS. 6, 8, and 10-12. It should be understood the graphical presentation of the streaming gas concentration data may vary in other embodiments or may be able to be changed via the user interface 105. For example, the graphical depiction plot the gas concentration data on the horizontal axis and the time on the vertical axis. In an embodiment, the user interface 105 and the display 110 are integrated into a single touch screen interface/display. The display may be configured as a color display or a black-and-white display.

Figure 3:
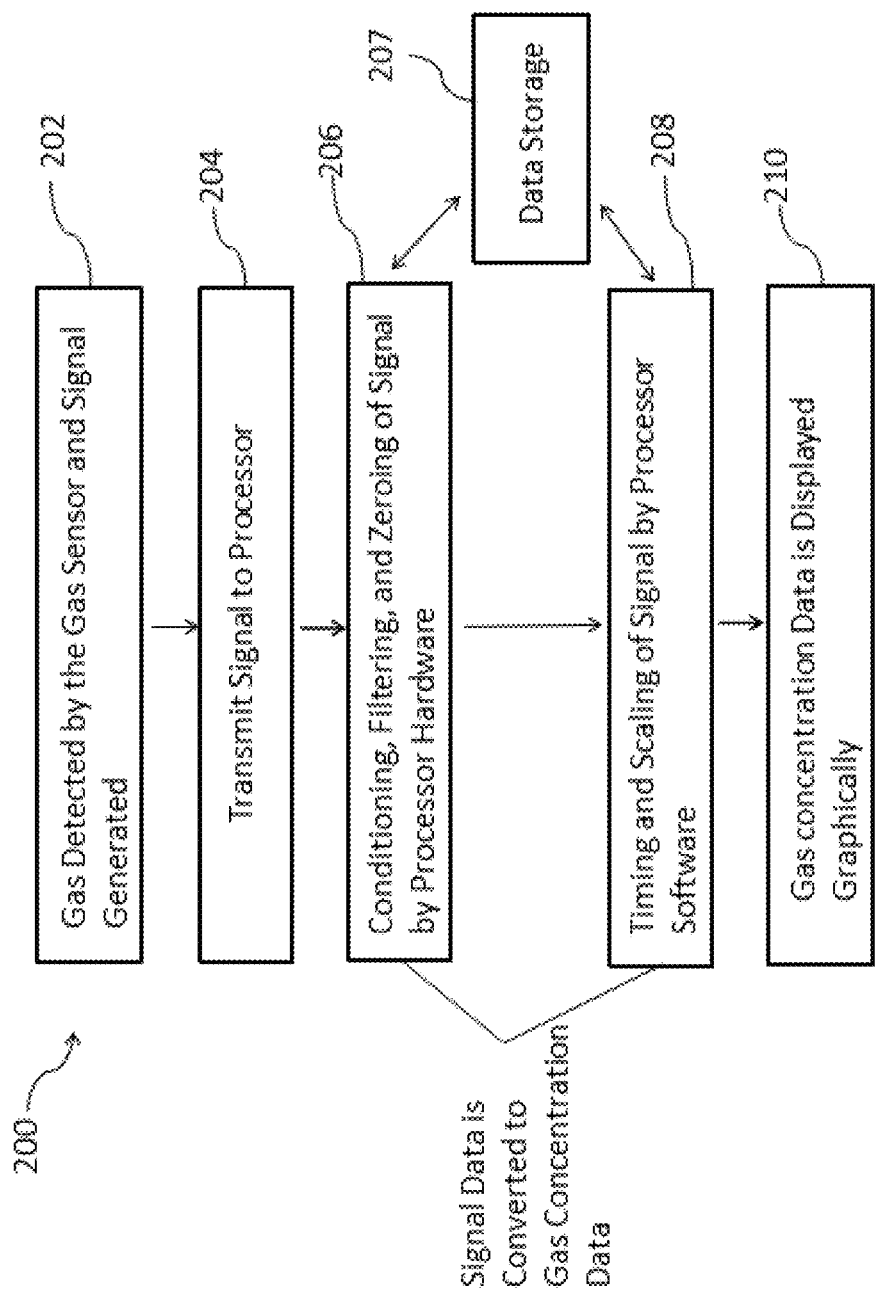
FIG. 3 illustrates a flow chart depicting an embodiment of the general control flow of the process for apparatus, methods, and systems for displaying gas concentration data.

FIG. 3 illustrates a flow chart generally depicting an embodiment of the process 200 for collecting and displaying gas concentration data according to one embodiment. The process begins at step 202 when a gas is detected by the gas sensor 115 (FIGS. 1-2) and a signal is generated, which corresponds to the detected gas concentration. The signal is then transmitted to the processor at step 204. Next, the processor hardware is responsible for conditioning, filtering, and zeroing the received signal at step 206. At step 208, timing and scaling of the signal is done by the processor software. It should be understood that the processing steps 206, 208 may be performed in any order and not necessarily in the order depicted in FIG. 3. The processing steps 206, 208 are responsible for converting the signal data into gas concentration data. In an embodiment, the processing steps 206, 208 may be performed by a central processing unit (CPU) and/or one or more microprocessor units. During the processing steps 206, 208, the signal data/gas concentration data may be stored and subsequently retrieved from a data storage 207. In an embodiment, the data storage 207 may comprise a memory unit that is part of the processor, however in other embodiments, the data storage 207 may comprise a memory unit that is separate from, but in electronic communication with the processor. The gas concentration data is then displayed graphically at step 210.

Figure 3A:
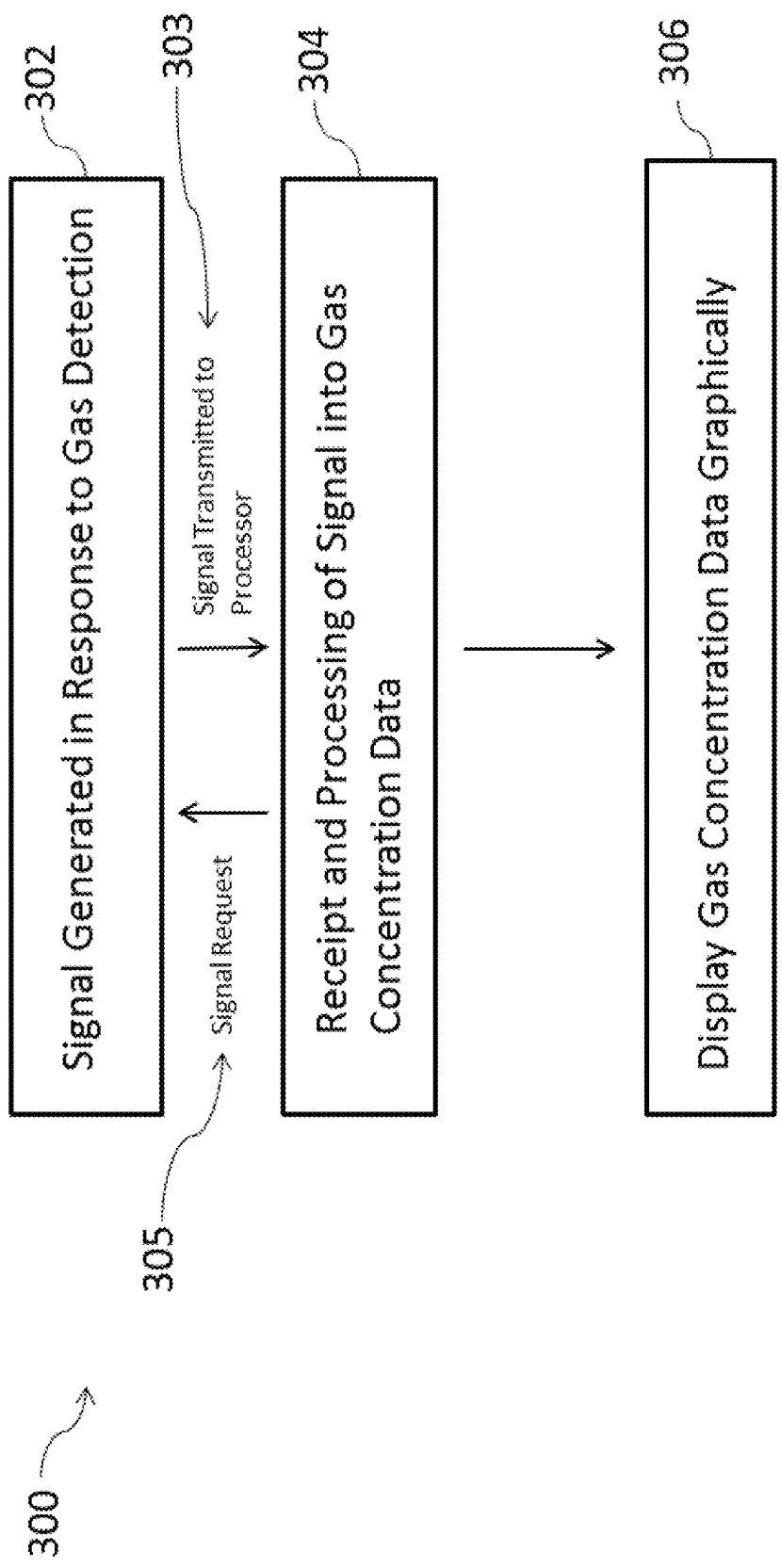
FIG. 3A illustrates a flow chart depicting an embodiment of the general control flow of the process for apparatus, methods, and systems for displaying gas concentration data.

As shown in FIG. 3A, another embodiment the process 300 for displaying gas concentration data comprises generating a signal in response to gas detection at step 302. The signal is transmitted to the processor at step 303 where it is received and converted into gas concentration data at step 304. At step 305, the processor continuously monitors or requests signal transmissions over a predetermined time period. In another embodiment, the processor continuously receives signals over a predetermined period of time without requesting them. It is understood that the time periods may be adjusted depending on the specific situation. In and embodiment, the predetermined time period may be set with the user interface 105 (FIGS. 1-2) and a timing element may be configured to stop signal requests by the processor or the receipt of signals by the processor after the predetermined time period has expired. In still another embodiment, the processor may receive signals continuously as long as the detector 100 (FIGS. 1-2) is turned on.

Lastly, the gas concentration data is displayed in step 306 in a streaming fashion on a graphical display, in a streaming fashion. The detection system is configured to continuously monitor and receive signals so that it may continuously update gas concentration data to display on the graphical display in a streaming fashion as gas levels are detected.

Figure 4:
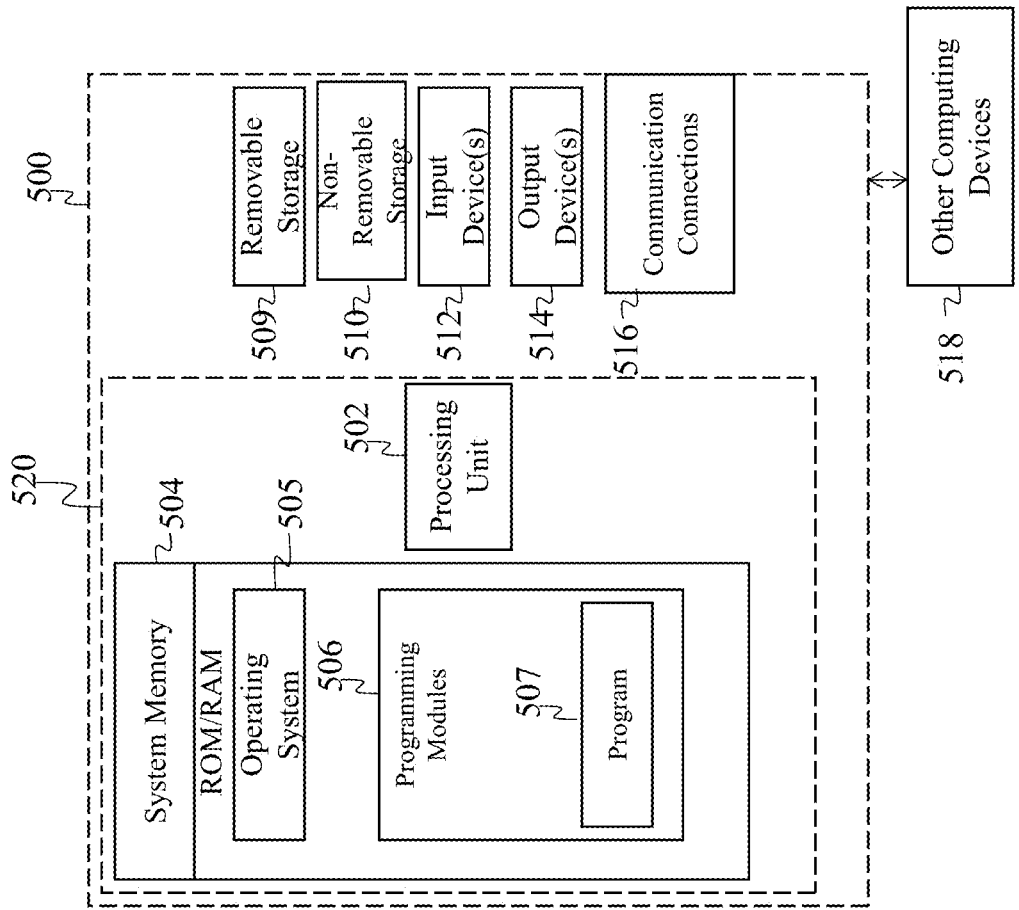
FIG. 4 illustrates a block diagram of an embodiment of a leak detection system with one or more computing devices.

FIG. 4 is a block diagram of a system for displaying gas concentration data including an example computing device 500 and other computing devices. Consistent with the embodiments described herein, the aforementioned actions performed by the leak detector may be implemented in a computing device, such as the computing device 500 of FIG. 4. Any suitable combination of hardware, software, or firmware may be used to implement the computing device 500. The aforementioned system, device, and processors are examples and other systems, devices, and processors may comprise the aforementioned computing device.

With reference to FIG. 4, a system consistent with an embodiment of the invention may include a plurality of computing devices, such as computing device 500. In an embodiment, computing device 500 may include at least one processing unit 502 and a system memory 504. Depending on the configuration and type of computing device, system memory 504 may comprise, but is not limited to, volatile (e.g. random access memory (RAM)), non-volatile (e.g. read-only memory (ROM)), flash memory, or any combination or memory. System memory 504 may include operating system 505, one or more programming modules 506 (such as program module 507). Operating system 505, for example, may be suitable for controlling computing device 500's operation. In one embodiment, programming modules 506 may include, for example, a program module 507. Furthermore, embodiments of the invention may be practiced in conjunction with a graphics library, other operating systems, or any other application program and is not limited to any particular application or system. This basic configuration is illustrated in FIG. 4 by those components within a dashed line 520.

The computing device 500 may have additional features or functionality. For example, the computing device 500 may also include additional data storage devices (removable and/or non-removable), such as, for example, magnetic disks, optical disks, or tape. Such additional storage is illustrated in FIG. 4 by a removable storage 509 and a non-removable storage 510. Computer storage media may include volatile and nonvolatile, removable and non-removable media implemented in any method or technology for storage of information, such as computer readable instructions, data structures, program modules, or other data. System memory 504, removable storage 509, and non-removable storage 510 are all computer storage media examples (i.e. memory storage). Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 500. Any such computer storage media may be part of device 500. Computing device 500 may also have input device(s) 512, such as a keyboard, a mouse, a pen, a sound input device, a camera, a touch input device, or other such input devices as would be necessary or improve the functionality of the detector 100 (FIGS. 1-2). Output device(s) 514, such as, a display, speakers, a printer, etc. may also be included. The aforementioned devices are only examples, and other devices, may be added or substituted.

Computing device 500 may also contain a communication connection 516 that may allow the device 500 to communicate with other computing devices 518, such as over a network in a distributed computing environment, for example, an intranet or the Internet. Communication connection 516 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media, such as a wired network or direct-wired connection, and wireless media, such as acoustic, radio frequency (RF), infrared, and other wireless media. The term computer readable media as used herein may include both computer storage media and communication media.

As stated above, a number of program modules and data files may be stored in system memory 504, including the operating system 505. While executing on the processing unit 502, programming modules 506 may perform processes including, for example, one or more of the methods shown in FIGS. 2-4 above. Computing device 502 may also include a graphics processing unit, which supplements the processing capabilities of processor 502 and which may execute programming modules 506, including all or a portion of those processes and methods shown and described in figures. The aforementioned processes are examples, and processor 502 may perform other processes. Other programming modules that may be used in accordance with embodiments of the present invention may include electronic mail and contacts applications, word processing applications, spreadsheet applications, database applications, slide presentation applications, drawing or computer-aided application programs, or other suitable programming modules that enhance or improve the functionality of the detector 100 (FIGS. 1-2).

Some embodiments may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Other embodiments may also be practiced using other technologies capable of performing logical operations, such as, for example, AND, OR, and NOT, including but not limited to mechanical, optical, fluidic, and quantum technologies. In addition, embodiments of the invention may be practiced within a general purpose computer or in any other circuits or systems.

Some embodiments, for example, are described above with reference to block diagrams and/or operational illustrations of methods, systems, and computer program products. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Furthermore, although some embodiments have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Example 1

Figure 5:
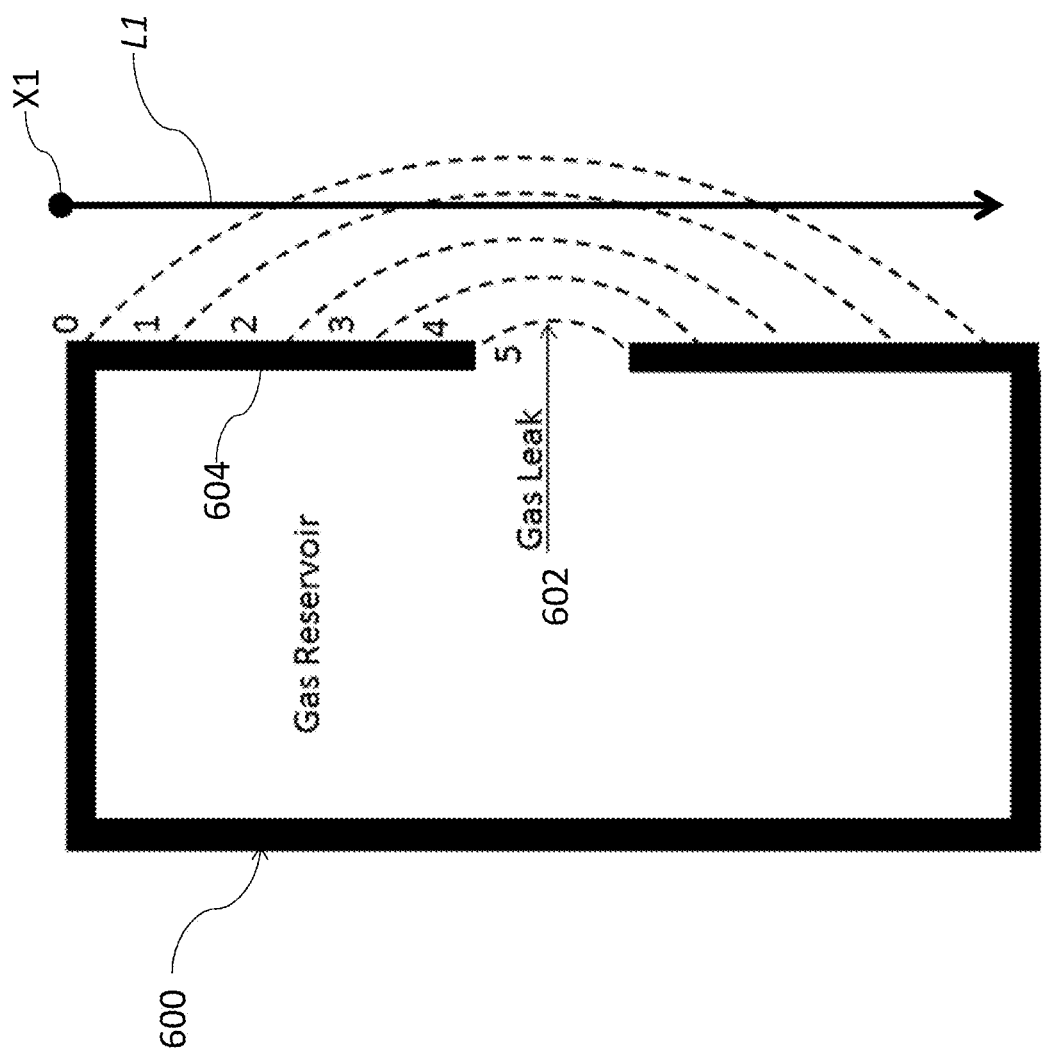
FIG. 5 illustrates a schematic depiction of a gas leak from a gas reservoir including isolines corresponding to theoretical gas concentrations and a detection path L1 beginning at location X1.

Referring to FIG. 5, a schematic representation of a gas reservoir 600 is shown having a very small break or leak 602 in one of its walls 604 that is undetectable to the naked eye. As the gas is emitted from the leak 602, a concentration gradient of gas forms outside of the gas reservoir 600 and is represented by isolines. Each isoline demarcates a theoretical gas concentration (1-5) such that locations between the isolines will have a gas concentration somewhere between the value of each bordering isoline. The area outside the isolines has a theoretical gas concentration value of zero (0). The gas reservoir 600 may be any container or conduit configured to hold, store, or transport a gaseous substance.

Figure 6:
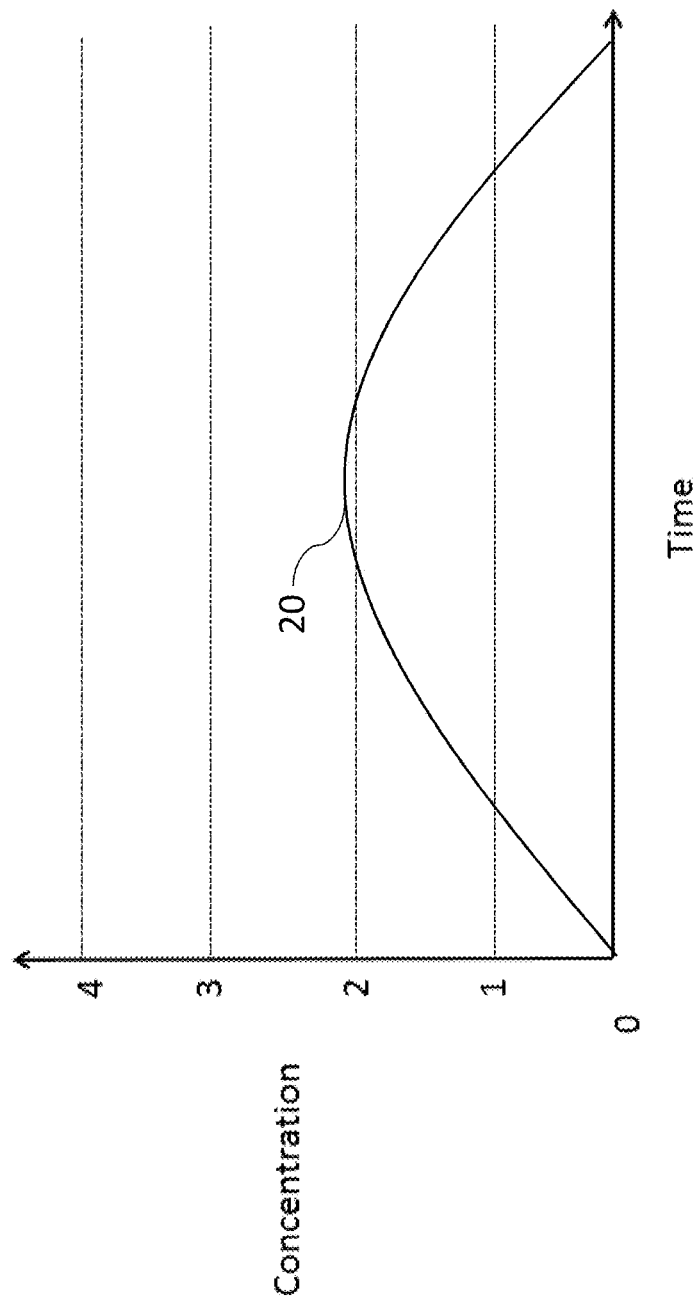
FIG. 6 illustrates a graphical depiction of the measured gas concentration as the gas leak detector moves along detection path L1 beginning at location X1.

As shown in FIG. 5, the detector begins measuring gas concentration at point X1. Over a period of time, the detector moves along detector path L1 away from point X1 in an effort to locate the gas leak 602. The gas concentration levels are displayed graphically as shown in FIG. 6. As shown the gas concentration values are plotted in relation to time, however in other modes the gas concentration values may be plotted in relation to another data point, such as location. Still referring to FIG. 6, the gas concentration data points are plotted in the form of a continuous line so that it is easy to determine when a peak gas concentration has been measured along the detection path L1. In practice, the detector could stop at or near the peak reading and begin to approach the reservoir 600 in order to further pinpoint the exact location of the leak.

Example II

Figure 7:
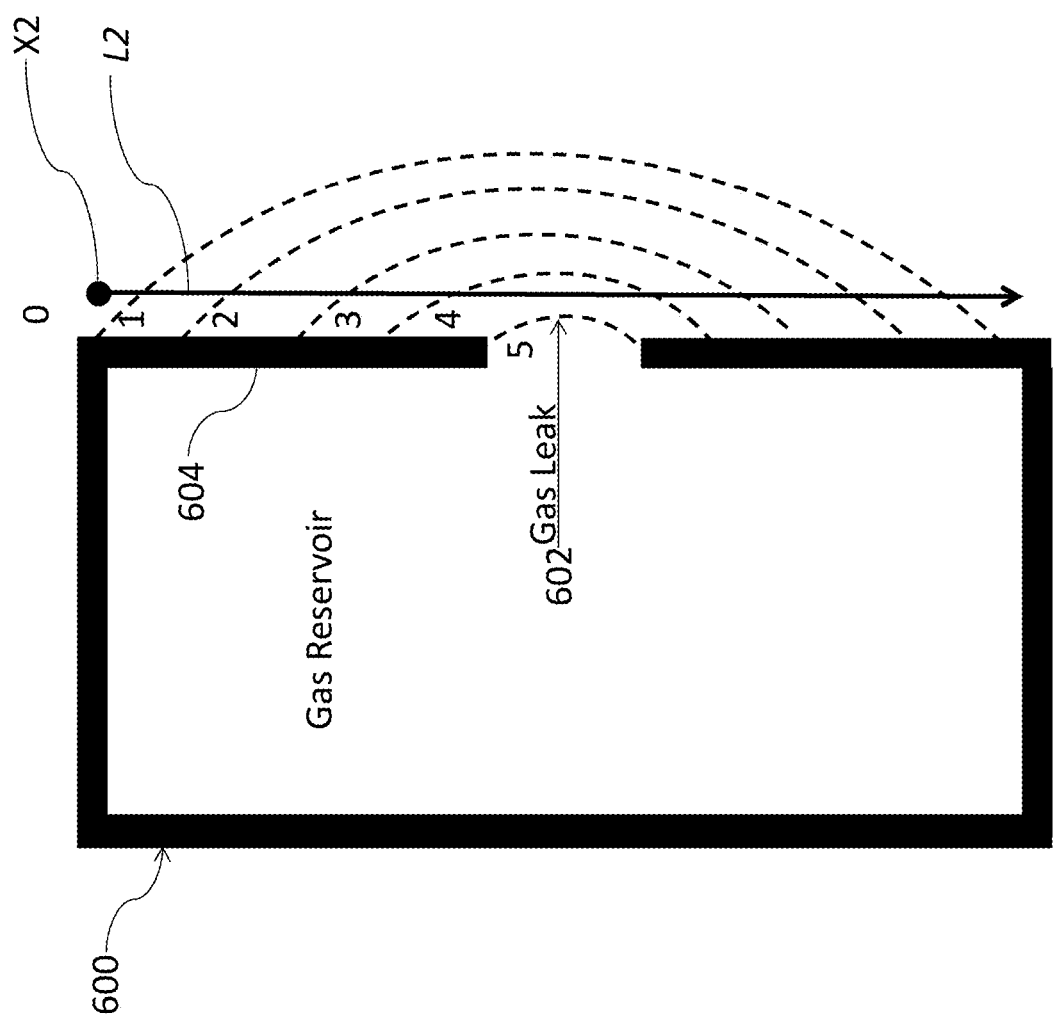
FIG. 7 illustrates the schematic depiction of the gas leak of FIG. 5 with a detection path L2 beginning at location X2.
Figure 8:
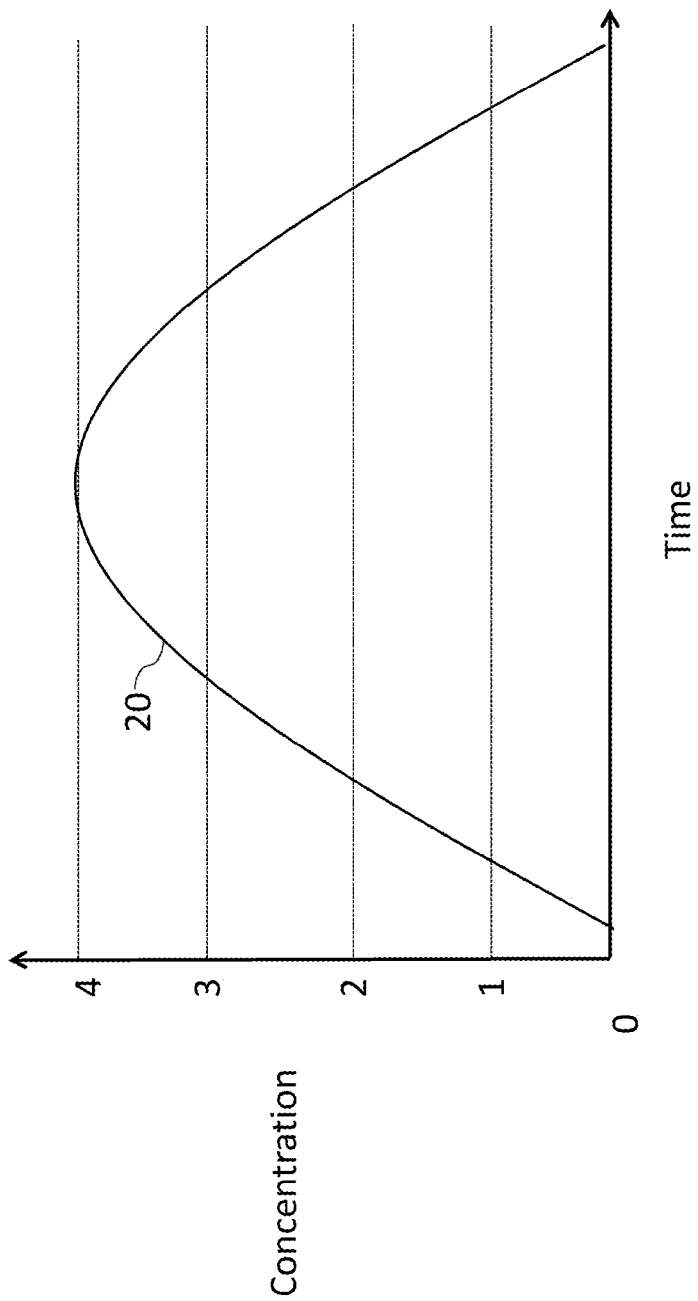
FIG. 8 illustrates a graphical depiction of the measured gas concentration as the gas leak detector moves along detection path L2 beginning as location X2.

FIG. 7 represents the same gas reservoir 600 and gas leak 602 scenario as in FIG. 5, however, in this example gas detection begins closer to the gas reservoir 600 as point X2 and continues along detector path L2 away from point X2. The gas concentration levels are displayed graphically as shown in FIG. 8. As shown the gas concentration values are plotted in relation to time, however, in other modes, the gas concentration values may be plotted in relation to another data point such as location. Still referring to FIG. 8, the gas concentration data points are plotted in the form of a continuous line so that it is easy to determine when a peak gas concentration has been achieved along the detection path L2. In practice, the detector could stop at or near the peak reading and begin to approach the reservoir 600 in order to further pinpoint the exact location of the leak. As shown, the peak gas concentration measured is greater than in Example I due to the closer proximity of the detector (FIGS. 1-2) to the leak.

Example III

Figure 9:
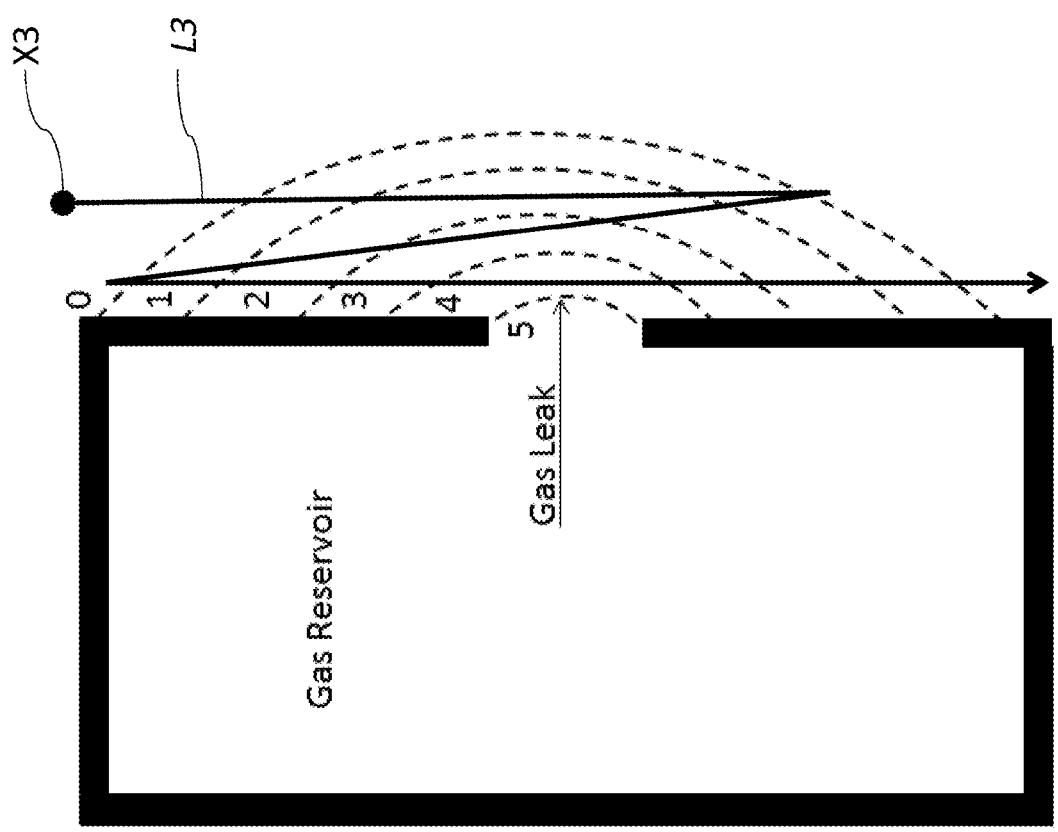
FIG. 9 illustrates the schematic depiction of the gas leak of FIG. 5 with a detection path L3 beginning at location X3.
Figure 10:
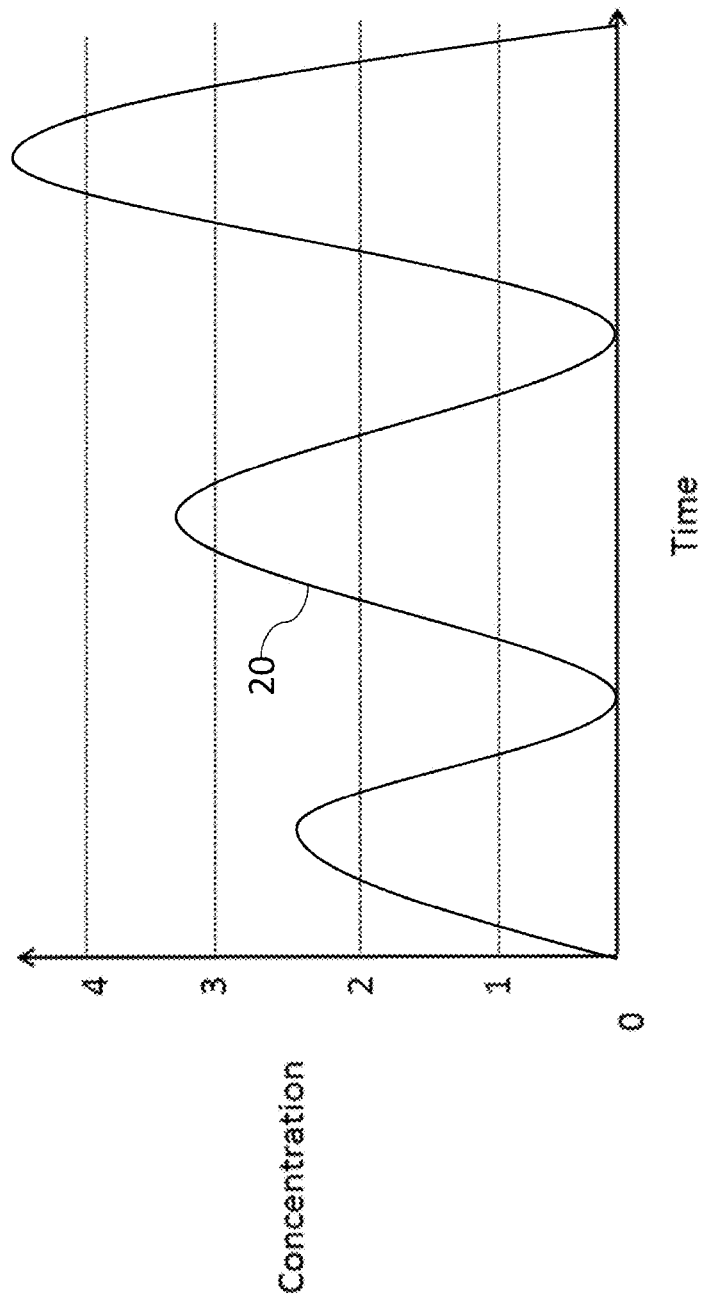
FIG. 10 illustrates a graphical depiction of the measured gas concentration as the gas leak detector moves along detection path L3 beginning at location X3.

FIG. 9 represents the same gas reservoir 600 and gas leak 602 scenario as in FIG. 5, however in this example gas detection begins away from the gas reservoir 600 at point X3 and moves closer to the gas reservoir along detector path L3 and away from point X3 in an effort to pinpoint the location of the gas leak 602. The gas concentration levels are displayed graphically, as shown in FIG. 10. As shown, the gas concentration values are plotted in relation to time, however, in other modes, the gas concentration values may be plotted in relation to another data point such, as location. Still referring to FIG. 10, the gas concentration data points are plotted in the form of a continuous line and exhibit here spikes corresponding to the three times that the detector passed in front of the gas leak 602. As the detector moves closer to the gas leak 602, the displayed gas concentration increases making it easier to pinpoint the exact location of the gas leak 602.

Figure 11:
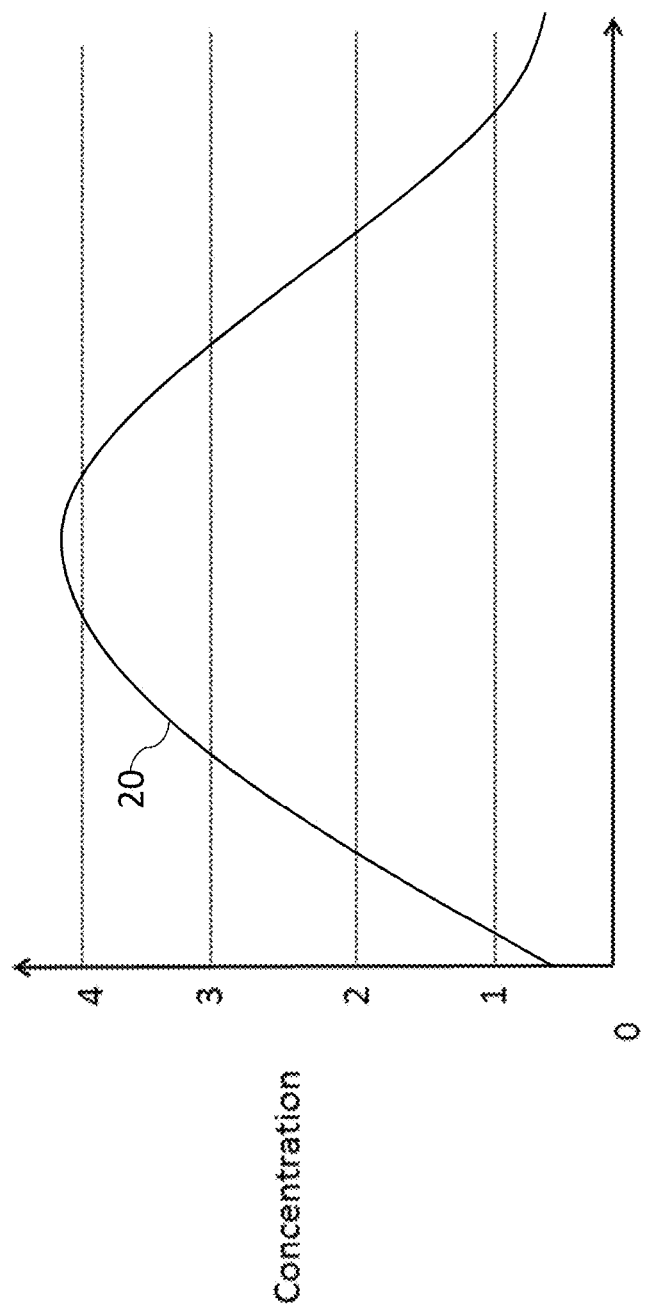
FIG. 11 illustrates a graphical depiction of the measured gas concentration as the gas leak detector moves along detection path L2 beginning at location X2 in relation to a determined baseline environmental concentration of gas.

In each of the above examples, the baseline gas concentration is zero (0), however in other embodiments, the gas that is the subject of the leak may already be present in the surrounding environment. Gases such as, for example, sulfur dioxide ($SO_2$), nitrogen oxides ($NO_x$), carbon monoxide (CO), volatile hydrocarbons like methane ($CH_4$) or propane ($C_3H_8$), may already be present in the ambient air of some heavily populated cities or industrial parks. Accordingly, the baseline gas concentration may not be zero (0). In an embodiment, the detector 100 (FIGS. 1-2) is configured to automatically detect an average environmental gas concentration. FIG. 11 represents the displayed gas concentration readings of FIG. 8 if the baseline concentration of the gas being detected were not zero (0). As shown, a spike in gas concentration is still visible when the detector 100 (FIGS. 1-2) is closest to the gas leak 602 while traveling along detector path L2. Accordingly, the disclosed system, methods and detector are configured to allow the user to find the leak source easily by providing a system that calibrates itself either automatically (default) or manually to the ambient, activates an alarm 112 (FIG. 1) when the detected gas concentration exceeds a threshold concentration, and can reset the alarm 112 (FIG. 1) as soon as there is detection. In another embodiment, the detector 100 (FIGS. 1-2) automatically "zeros out" or corrects for the average environmental gas concentration.

Figure 12:
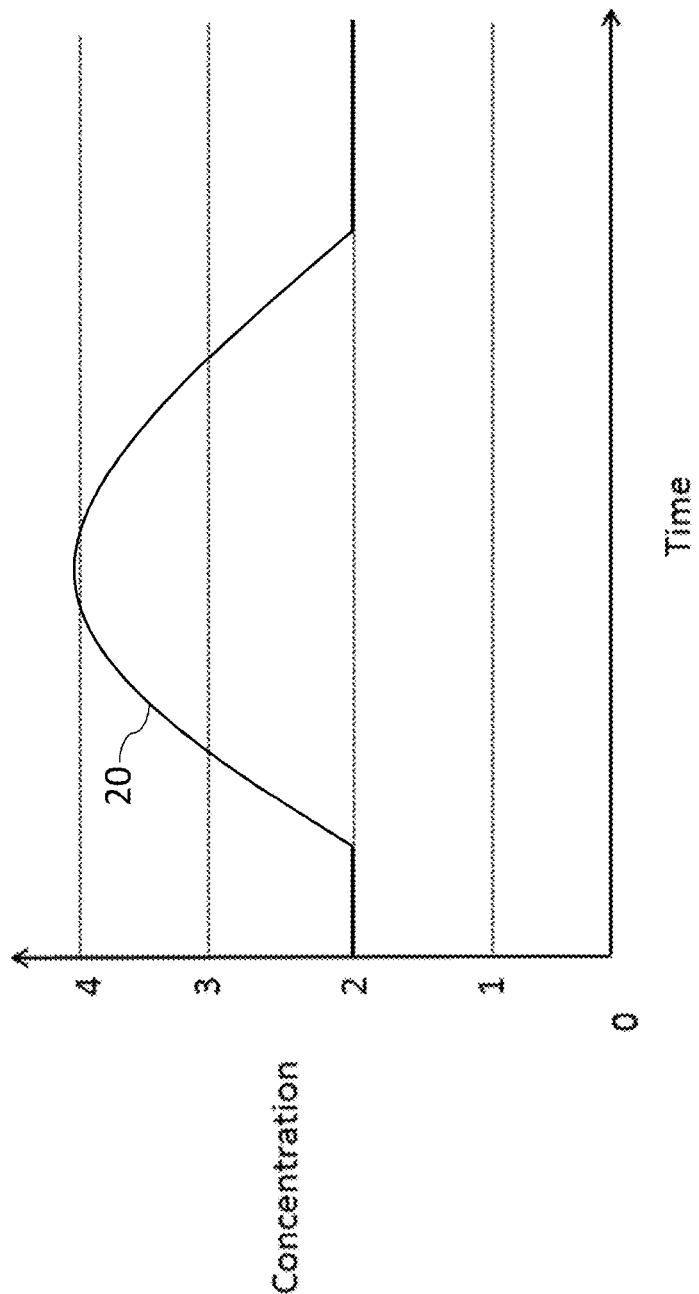
FIG. 12 illustrates a graphical depiction of the measured gas concentration as the gas leak detector moves along detection path L2 beginning at location X2 when the gas leak detector is programmed to only display gas concentration readings above two (2).

In an embodiment, the detector 100 (FIGS. 1-2) may be programmed to only display gas concentration levels that are above a predetermined value. FIG. 12 illustrates the displayed gas concentration readings of FIG. 8 if the detector were programmed to only display gas concentration readings above two (2). As shown, the spike in gas concentration is more compact which can make it easier to find the source of the gas leak. When the gas concentration is at or below two (2), the trace line of the graph remains at a constant value.

In other embodiments, the detector 100 (FIGS. 1-2) may be configured to correct for wind currents, which may push a plume of gas away from the actual gas leak and would provide a false indication of the actual location of the gas leak. In another embodiment, the detector 100 (FIGS. 1-2) may be configured to plot gas concentration data relative to multiple variables at once such as time, location, or distance. The system is configured, such that the graphical element updates each time a new signal is received and displays in a continuous streaming like fashion so that a user and can visually see on the screen the value of the signal over a period of time. In the present embodiment, the display may include a y axis that corresponds to the sensor signal of the gas concentration level. Since the display (in this mode) is based on a time period in a streaming fashion, the previous leak level sensed will be displayed helping the user to determine where the maximum level of gas is present and thereby pinpointing the source of the leak.

In one embodiment, the detector (FIGS. 1-2) includes a feature so that the display can be adjusted to increase or decrease the scale of the display. For example, a user may use controls to "zoom in" or "zoom out" so that the quantity of units of measurement displayed on the axis corresponding to the gas concentration (in the present embodiment this is the y-axis) is adjusted so that the user can pinpoint larger or smaller leaks. Additionally, the display may also be adjusted so that the units of time displayed on the axis corresponding to the period of time (in the present embodiment this is the x-axis) can be increased or decreased so that a user can "zoom in" or "zoom out" to pinpoint larger or smaller leaks. Other display adjustment options are also possible including concentration measurement frequency, brightness, contrast, and other such display adjustment options in order to provide for an adjustable display for a variety of applications.

While the present invention has been particularly shown and described with reference to certain exemplary embodiments, it will be understood by one skilled in the art that various changes in detail may be effected therein without departing from the spirit and scope of the invention that can be supported by the written description and drawings. Further, where exemplary embodiments are described with reference to a certain number of elements it will be understood that the exemplary embodiments can be practiced utilizing either less than or more than the certain number of elements.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for displaying gas concentration values on a graphical display of a leak detector, the method comprising:
   detecting a presence of a gas using a gas sensor;
   generating a signal from the gas sensor;
   transmitting the signal from the gas sensor to a processor;
   processing a received signal from the gas sensor to determine a gas concentration value;
   associating the gas concentration with a corresponding time stamp;
   storing the gas concentration value and the corresponding time stamp;
   monitoring transmitted signals from the gas sensor over a predetermined time period and storing determined gas concentration values and corresponding time stamps;
   determining an average environmental gas concentration; and
   displaying the gas concentration values relative to the average environmental gas concentration and corresponding time stamps graphically as they are determined, wherein newly determined gas concentration values and corresponding time stamps are displayed in relation to previously determined gas concentration values and time stamps in streaming fashion.

2. A method for displaying gas concentration values on a graphical display of a leak detector, the method comprising:
   detecting a presence of a gas using a gas sensor;
   generating a signal from the gas sensor;
   transmitting the signal from the gas sensor to a processor;
   processing a received signal from the gas sensor to determine a gas concentration value;
   storing the gas concentration value;
   monitoring transmitted signals from the gas sensor over a predetermined time period and storing determined gas concentration values;
   determining an average environmental gas concentration; and
   displaying the gas concentration values relative to the average environmental gas concentration graphically as they are determined, wherein newly determined gas concentration values are displayed in relation to previously determined gas concentration values in streaming fashion.

3. The method of claim 2, further comprising associating the gas concentration value with a corresponding time stamp.

4. The method of claim 2, further comprising collecting location data associated with the gas concentration value.

5. The method of claim 4, further comprising graphically displaying the gas concentration values and corresponding location data.

6. The method of claim 2 wherein the gas concentration values are displayed as a continuous trace line.

7. The method of claim 6, wherein the continuous trace line remains at a constant value unless the signal from the gas sensor corresponds to the gas concentration value that exceeds a predetermined value.

8. The method of claim 2, further comprising triggering an alarm when any one of the gas concentration values exceeds a predetermined value.

9. A gas leak detector comprising:
   a housing at least partially surrounding,
     a gas sensor configured to generate a signal in response to a presence of a gas,
     a processor in communication with the gas sensor and configured to receive the signal generated by the gas sensor and convert the signal to gas concentration data, wherein the processor is configured to continuously monitor the signal over a predetermined period,
     a memory unit in communication with the processor and configured to store gas concentration data, and wherein the stored gas concentration data is accessible by the processor, a display in communication with the processor and configured to display gas concentration data as the gas concentration data is obtained, wherein an average environmental gas concentration is determined, wherein newly obtained gas concentration data is displayed graphically in a streaming manner relative to the average environmental gas concentration along with previously displayed gas concentration data relative to the average environmental gas concentration.

10. The gas leak detector of claim 9, further comprising a user interface configured to allow a user to select the gas concentration data to be displayed.

11. The gas leak detector of claim 9, wherein the gas concentration data comprises a gas concentration value and corresponding location data.

12. The gas leak detector of claim 9, wherein the gas concentration data comprises a gas concentration value and a corresponding time stamp.

13. The gas leak detector of claim 9, further comprising an alarm configured to trigger when a gas concentration value exceeds a predetermined value.

* * * * *